United States Patent
Fan et al.

(10) Patent No.: US 12,024,601 B2
(45) Date of Patent: Jul. 2, 2024

(54) POLYVINYL ALCOHOL HYDROGEL HAVING ASYMMETRIC PORE SIZE

(71) Applicant: NORTHWEST UNIVERSITY, Shaanxi (CN)

(72) Inventors: Daidi Fan, Shaanxi (CN); Yang Li, Shaanxi (CN); Chenhui Zhu, Shaanxi (CN); Chanyuan Yang, Shaanxi (CN); Liping Jia, Shaanxi (CN); Xiaoxuan Ma, Shaanxi (CN); Jianya Yan, Shaanxi (CN)

(73) Assignee: NORTHWEST UNIVERSITY, Shaanxi (CN)

( * ) Notice: Subject to any disclaimer, the term of this patent is extended or adjusted under 35 U.S.C. 154(b) by 434 days.

(21) Appl. No.: 17/427,296

(22) PCT Filed: Jan. 31, 2019

(86) PCT No.: PCT/CN2019/074237
§ 371 (c)(1),
(2) Date: Jul. 30, 2021

(87) PCT Pub. No.: WO2020/155041
PCT Pub. Date: Aug. 6, 2020

(65) Prior Publication Data
US 2022/0145014 A1 May 12, 2022

(51) Int. Cl.
| C08J 3/00 | (2006.01) |
| A61L 15/24 | (2006.01) |
| A61L 15/42 | (2006.01) |
| C08J 3/075 | (2006.01) |
| C08J 9/28 | (2006.01) |
| C08L 1/00 | (2006.01) |
| C08L 5/00 | (2006.01) |
| C08L 29/04 | (2006.01) |

(52) U.S. Cl.
CPC ............ *C08J 3/075* (2013.01); *A61L 15/24* (2013.01); *A61L 15/425* (2013.01); *C08J 9/283* (2013.01); *C08L 29/04* (2013.01); *C08J 2201/0484* (2013.01); *C08J 2207/10* (2013.01); *C08J 2329/04* (2013.01); *C08J 2401/28* (2013.01); *C08J 2405/04* (2013.01); *C08J 2405/08* (2013.01)

(58) Field of Classification Search
CPC ........ A61L 15/425; A61L 15/60; C08J 3/075; C08J 2205/022
See application file for complete search history.

(56) References Cited

U.S. PATENT DOCUMENTS

| 7,235,592 B2 * | 6/2007 | Muratoglu ................. C08J 3/28 525/61 |
| 2005/0049323 A1 * | 3/2005 | Gvozdic .................... C08J 5/04 521/64 |
| 2006/0079597 A1 * | 4/2006 | Muratoglu ................. C08J 3/28 522/178 |
| 2009/0062408 A1 * | 3/2009 | Liu ......................... A61L 27/52 516/104 |
| 2016/0038632 A1 * | 2/2016 | Shah ....................... A61L 27/18 514/8.1 |

FOREIGN PATENT DOCUMENTS

| CN | 101181642 | 5/2008 |
| CN | 101249275 | 8/2008 |
| CN | 103977448 | 8/2014 |
| WO | 2017/100878 | 6/2017 |

OTHER PUBLICATIONS

Luo et al., "Gradient Porous Elastic Hydrogels with Shape-Memory Property and Anisotropic Responses for Programmable Locomotion", Oct. 2015, Advanced Functional Materials, vol. 25, Issue 47, pp. 7272-7279 (Year: 2015).*
International Search Report issued Sep. 25, 2019 in International (PCT) Application No. PCT/CN2019/074237.
Ling et al., "Preparation and Properties of Asymmetric PVA-Chitosan-Gelatin Sponge", Journal of Wuhan University of Technology, vol. 51, No. 4, Aug. 2005, pp. 443-447, English abstract.

* cited by examiner

*Primary Examiner* — Melissa A Rioja
(74) *Attorney, Agent, or Firm* — Wenderoth, Lind & Ponack, L.L.P.

(57) ABSTRACT

The present invention relates to a polyvinyl alcohol hydrogel having an asymmetric pore size. the pore size of the upper surface of the polyvinyl alcohol hydrogel is 1-30 μm, the pore size of lower surface thereof is 50-300 μm, and the pore size of the hydrogel gradually increases from the upper surface to the lower surface. The polyvinyl alcohol hydrogel in the present invention has excellent biocompatibility, and has functions of blocking bacteria, anti-adhesion, the absorption of exudate, promoting wound healing, observing in situ of wound healing process and the like.

13 Claims, 1 Drawing Sheet

POLYVINYL ALCOHOL HYDROGEL HAVING ASYMMETRIC PORE SIZE

TECHNICAL FIELD

The invention belongs to the field of biomedical materials, and particularly relates to a sponge-like hydrogel dressing with an asymmetric aperture size, and a preparation method thereof.

BACKGROUND

Hydrogel is a water-insoluble soft material with water retention. This material has a soft texture, can maintain a certain shape, and absorb a large amount of water.

The good water absorption of hydrogel makes it potential for wound dressing applications. However, the currently clinically used hydrogel dressings can only be used as moisturizing and isolation protective materials, and they cannot meet the clinical requirements of both absorbing exudate and preventing external bacteria from infiltrating wounds as a wound dressing.

From the structure of the hydrogel material, there is a contradiction between the function of absorbing exudate and the function of preventing bacteria, since the aperture size of the hydrogel should be as large as possible to absorb the exudate, while the aperture size of the hydrogel should be as small as possible to prevent bacteria.

In order to balance the function of the hydrogel material for absorbing the exudate and preventing bacteria, the researchers constructed a hydrogel with a double-layer structure—a second layer of hydrogel was prepared in situ on the surface of the first layer of hydrogel, with the aperture size at the junction of the two layers changing suddenly, wherein the lower layer has a large pore and a loose structure suitable for water absorption, and the upper layer has a small pore and a compact structure suitable for blocking bacteria. However, the major disadvantage of the double-layer structure hydrogel is that: the bonding at the interface between the two layers is weak, and the two layers are easy to separate and fall off during use, which limits its clinical application. In addition, researchers have also tried to use chemical hydrothermal synthesis, electrospinning and other techniques to prepare hydrogels with heterogeneous structures, but the preparation conditions are complex and difficult to control, thus large-scale preparation cannot be achieved, and the residues of toxic chemical crosslinking agents do not meet the requirements for clinical applications. Moreover, the aperture sizes of the heterogeneous structure hydrogels in the prior art are all changed stepwise rather than gradually. It should be noted that the heterogeneous structure hydrogel refers to a hydrogel with uneven aperture sizes, and the hydrogel may be a single layer or a double-layer structure.

Therefore, how to prepare a monolayer hydrogel with asymmetric aperture size by a simple and easy-to-control method is a difficult problem that must be solved, when hydrogel materials are used as wound dressings.

CONTENTS OF THE INVENTION

In view of the above-mentioned problems in the prior art, an object of the present invention is to provide a monolayer hydrogel with asymmetric apertures and a preparation method thereof.

The invention includes:

1. A monolayer hydrogel with an asymmetric aperture size, wherein the aperture size of upper surface of the monolayer hydrogel is 1-30 µm, preferably 5-20 µm; and the aperture size of lower surface of the monolayer hydrogel is 50-300 µm, preferably 80-150 µm.

In this specification, the lower surface of the hydrogel refers to the surface with the larger aperture size that is in contact with the wound when it is used as a wound dressing; and for the hydrogel the other surface with the smaller aperture size is the upper surface. The asymmetric aperture size of the hydrogel means that the aperture sizes of the upper and lower surfaces are different.

2. The monolayer hydrogel according to item 1, which is a sponge-like polyvinyl alcohol hydrogel.

3. The monolayer hydrogel according to item 1 or 2, the aperture sizes of the monolayer hydrogel gradually increase from the upper surface to the lower surface. In this specification, "gradually increase" refers to the continuous increase of the aperture size in the longitudinal section direction (the thickness direction of the hydrogel) from top to bottom (rather than a stepwise increase). For example, for any aperture of the hydrogel, taking any two points A and B, with point A on the top and point B on the bottom, so that the aperture size of point B is larger than the aperture size of point A.

4. A method for preparing the monolayer hydrogel according to any one of items 1-3, which comprising the following steps:

(1) dissolving respectively a water-soluble tackifier and polyvinyl alcohol in water with a certain content, so as to obtain an water-soluble tackifier aqueous solution and an polyvinyl alcohol aqueous solution respectively; wherein the viscosity of the water-soluble tackifier is 200-10000 cP;

(2) preparing a warm mixed solution of the water-soluble tackifier aqueous solution and the polyvinyl alcohol aqueous solution at a certain mixing ratio;

(3) dissolving polyethylene glycol powder into the warm mixed solution with a certain content, so that it is completely dissolved to be a clear solution, thereby obtaining a hydrogel preparation solution;

(4) pouring the hydrogel preparation solution into a template and performing low-temperature freezing to obtain the monolayer hydrogel.

In this specification, a water-soluble tackifier refers to a substance that may be dissolved in water to make its aqueous solution have a certain viscosity, for example: hyaluronic acid, sodium alginate, sodium carboxymethyl cellulose, chondroitin sulfate, keratin sulfate, and so on. In one embodiment of the present invention, the water-soluble tackifier aqueous solution consists of a water-soluble tackifier and water. In one embodiment of the present invention, the polyvinyl alcohol aqueous solution consists of polyvinyl alcohol and water. In one embodiment of the present invention, the warm mixed solution consists of a water-soluble tackifier, polyvinyl alcohol and water. In one embodiment of the present invention, the hydrogel preparation solution consists of a water-soluble tackifier, polyvinyl alcohol, polyethylene glycol, and water.

5. The method according to item 4, wherein the water-soluble tackifier is selected from the group consisting of: hyaluronic acid, sodium alginate, sodium carboxymethyl cellulose, chondroitin sulfate, and keratan sulfate.

6. The method according to item 4, wherein the viscosity of the water-soluble tackifier is 200-10000 cP.

7. The method according to item 4, wherein the content of the water-soluble tackifier in the water-soluble tackifier aqueous solution is 0.4-3.6 wt %.
8. The method according to item 4, wherein the number-average molecular weight of the polyvinyl alcohol is 70,000-140,000.
9. The method according to item 4, wherein the content of polyvinyl alcohol in the polyvinyl alcohol aqueous solution is 12-30 wt %.
10. The method according to item 4, wherein the number-average molecular weight of the polyethylene glycol is 600-4000.
11. The method according to item 4, wherein the content of polyethylene glycol in the hydrogel preparation solution is 4.5-12 wt %.
12. The method according to item 4, wherein the temperature of the warm mixed solution is 70-95° C.
13. The method according to item 4, wherein the temperature of the low-temperature freezing is −14° C. to −24° C., and the time is 6-30 hours.
14. The method according to item 4, further comprising a step (3-1) between the step (3) and step (4): placing the hydrogel preparation solution at room temperature for 1-200 minutes.
15. The method according to item 4, wherein in the step (2), the mixing ratio of the water-soluble tackifier aqueous solution and polyvinyl alcohol aqueous solution is 1:1-5:1.

In addition, surprisingly the inventors also found that the above-mentioned monolayer hydrogel may also be used to prepare a double-layer hydrogel with tightly bonded upper and lower layers and seamless butt joints; since a hydrogen bond crosslink is formed by the component of this hydrogel at the junction of the two layers. This double-layer hydrogel is not easy to separate and fall off when used as a wound dressing.

Accordingly, the present invention also includes:
16. A method for preparing a double-layer hydrogel, comprising the following steps:
   (1) preparing the monolayer hydrogel according to the method of any one of items 4-14;
   (2) preparing the hydrogel preparation solution according to steps (1)-(3) of the method of any one of items 4-14;
   (3) pouring the hydrogel preparation solution of the above step (2) on the lower surface of the monolayer hydrogel prepared in the above step (1) in a normal temperature state, and then performing low-temperature freezing to obtain a double-layer hydrogel.

For example, a monolayer hydrogel with smaller aperture size may be prepared first, and then the hydrogel preparation solution used to prepare another monolayer hydrogel with larger aperture size is poured on the lower surface of the monolayer hydrogel with smaller aperture size.

17. The method according to item 16, wherein the temperature of the low-temperature freezing is −14° C. to −24° C., and the time is 6-30 hours.

The hydrogel according to the present invention has excellent biocompatibility, and has functions including blocking bacteria, preventing adhesion, absorbing exudate, promoting wound healing, and observing wound healing process in situ.

BRIEF DESCRIPTION OF THE DRAWINGS

FIG. 1a is a scanning electron micrograph of the lower surface aperture size of a monolayer hydrogel; FIG. 1b is a scanning electron micrograph of the upper surface; FIG. 1c is a scanning electron micrograph showing a longitudinal section of the monolayer hydrogel.

FIG. 2a is a scanning electron micrograph of the upper surface aperture size of the double-layer hydrogel; FIG. 2b is a scanning electron micrograph of the lower surface; and FIG. 2c is a scanning electron micrograph showing a longitudinal section of the double-layer hydrogel.

FIG. 3a shows a freeze-dried sample before shearing; FIG. 3b shows a freeze-dried sample after shearing; FIG. 3c shows a wet sample before shearing. FIG. 3d shows a wet sample after shearing.

SPECIFIC EMBODIMENTS OF THE INVENTION

Figure 1:
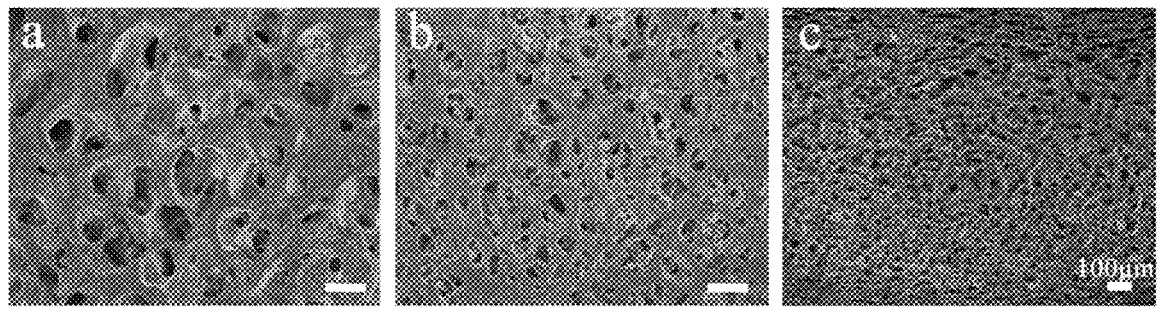
FIG. 1 is a scanning electron micrograph of the monolayer hydrogel prepared in the examples.

In this specification, if there is no special mention, % means weight percentage.

Example 1

Step 1: Sodium carboxymethyl cellulose and polyvinyl alcohol are respectively dissolved in deionized water with a content of 2.4% and 28% to obtain the uniform clear solutions;

Step 2: Polyethylene glycol powder is dissolved in a 1:1 mixed solution of the Step 1 solutions with a content of 7.5% at 80° C., to make it completely dissolved to be a clear solution;

Step 3: The mixed solution prepared in Step 2 is placed at room temperature for 50 minutes, then pouring it into a template, putting in a refrigerator at −20° C. for cross-linking, and taking it out of the refrigerator after freezing for 6 hours to obtain a hydrogel; circulating the freezing process for 4 times.

In Step 1, the molecular weight of polyvinyl alcohol is 95,000, and the viscosity of sodium carboxymethyl cellulose is 8,000 cP.

In Step 2, the molecular weight of polyethylene glycol is 1,500.

Example 2

Step 1: Sodium carboxymethyl cellulose and polyvinyl alcohol are respectively dissolved in deionized water with a content of 3.2% and 18% to obtain the uniform clear solutions;

Step 2: Polyethylene glycol powder is dissolved in a 1:1 mixed solution of the Step 1 solutions with a content of 7.0% at 85° C., to make it completely dissolved to be a clear solution;

Step 3: The mixed solution prepared in Step 2 is placed at room temperature for 80 minutes, then pouring it into a template, putting in a refrigerator at −22° C. for cross-linking, and taking it out of the refrigerator after freezing for 14 hours to obtain a hydrogel; circulating the freezing process for one time.

In Step 1, the molecular weight of polyvinyl alcohol is 80,000, and the viscosity of sodium carboxymethyl cellulose is 5,500 cP.

In Step 2, the molecular weight of polyethylene glycol is 4,000.

Example 3

Step 1: Sodium carboxymethyl cellulose and polyvinyl alcohol are respectively dissolved in deionized water with a content of 1.4% and 19% to obtain the uniform clear solutions;
Step 2: Polyethylene glycol powder is dissolved in a 2:1 mixed solution of the Step 1 solutions with a content of 10% at 90° C., to make it completely dissolved to be a clear solution;
Step 3: The mixed solution prepared in Step 2 is placed at room temperature for 10 minutes, then pouring it into a template, putting in a refrigerator at −18° C. for crosslinking, and taking it out of the refrigerator after freezing for 20 hours to obtain a hydrogel; circulating the freezing process for 2 times.
In Step 1, the molecular weight of polyvinyl alcohol is 100,000, and the viscosity of sodium carboxymethyl cellulose is 9,300 cP.
In Step 2, the molecular weight of polyethylene glycol is 3,000.

Example 4

Step 1: Hyaluronic acid and polyvinyl alcohol are respectively dissolved in deionized water with a content of 0.8% and 22% to obtain the uniform clear solutions;
Step 2: Polyethylene glycol powder is dissolved in a 1:1 mixed solution of the Step 1 solutions with a content of 10% at 85° C., to make it completely dissolved to be a clear solution;
Step 3: The mixed solution prepared in Step 2 is placed at room temperature for 30 minutes, then pouring it into a template, putting in a refrigerator at −18° C. for crosslinking, and taking it out of the refrigerator after freezing for 20 hours to obtain a hydrogel; circulating the freezing process for 2 times.
In Step 1, the molecular weight of polyvinyl alcohol is 120,000, and the viscosity of hyaluronic acid is 1,000 cP.
In Step 2, the molecular weight of polyethylene glycol is 2,000.

Example 5

Step 1: Hyaluronic acid and polyvinyl alcohol are respectively dissolved in deionized water with a content of 1.8% and 19% to obtain the uniform clear solutions;
Step 2: Polyethylene glycol powder is dissolved in a 1:1 mixed solution of the Step 1 solutions with a content of 8.5% at 90° C., to make it completely dissolved to be a clear solution;
Step 3: The mixed solution prepared in Step 2 is placed at room temperature for 20 minutes, then pouring it into a template, putting in a refrigerator at −22° C. for crosslinking, and taking it out of the refrigerator after freezing for 18 hours to obtain a hydrogel; circulating the freezing process for 4 times.
In Step 1, the molecular weight of polyvinyl alcohol is 140,000, and the viscosity of hyaluronic acid is 800 cP.
In Step 2, the molecular weight of polyethylene glycol is 1,500.

Example 6

Step 1: Hyaluronic acid and polyvinyl alcohol are respectively dissolved in deionized water with a content of 1.0% and 24% to obtain the uniform clear solutions;
Step 2: Polyethylene glycol powder is dissolved in a 2:1 mixed solution of the Step 1 solutions with a content of 7.5% at 80° C., to make it completely dissolved to be a clear solution;
Step 3: The mixed solution prepared in Step 2 is placed at room temperature for 10 minutes, then pouring it into a template, putting in a refrigerator at −18° C. for crosslinking, and taking it out of the refrigerator after freezing for 20 hours to obtain a hydrogel; circulating the freezing process for 2 times.
In Step 1, the molecular weight of polyvinyl alcohol is 100,000, and the viscosity of hyaluronic acid is 600 cP.
In Step 2, the molecular weight of polyethylene glycol is 4,000.

Example 7

Step 1: Sodium alginate and polyvinyl alcohol are respectively dissolved in deionized water with a content of 0.4% and 19% to obtain the uniform clear solutions;
Step 2: Polyethylene glycol powder is dissolved in a 3:1 mixed solution of the Step 1 solutions with a content of 8.0% at 90° C., to make it completely dissolved to be a clear solution;
Step 3: The mixed solution prepared in Step 2 is placed at room temperature for 40 minutes, then pouring it into a template, putting in a refrigerator at −20° C. for crosslinking, and taking it out of the refrigerator after freezing for 22 hours to obtain a hydrogel; circulating the freezing process for 3 times.
In Step 1, the molecular weight of polyvinyl alcohol is 90,000, and the viscosity of sodium alginate is 600 cP.
In Step 2, the molecular weight of polyethylene glycol is 3,000.

Example 8

Step 1: Sodium alginate and polyvinyl alcohol are respectively dissolved in deionized water with a content of 1.4% and 24% to obtain the uniform clear solutions;
Step 2: Polyethylene glycol powder is dissolved in a 1:1 mixed solution of the Step 1 solutions with a content of 9.0% at 85° C., to make it completely dissolved to be a clear solution;
Step 3: The mixed solution prepared in Step 2 is placed at room temperature for 5 minutes, then pouring it into a template, putting in a refrigerator at −22° C. for crosslinking, and taking it out of the refrigerator after freezing for 16 hours to obtain a hydrogel; circulating the freezing process for 3 times.
In Step 1, the molecular weight of polyvinyl alcohol is 100,000, and the viscosity of sodium alginate is 800 cP.
In Step 2, the molecular weight of polyethylene glycol is 2,000.

Example 9

Step 1: Sodium alginate and polyvinyl alcohol are respectively dissolved in deionized water with a content of 1.0% and 20% to obtain the uniform clear solutions;
Step 2: Polyethylene glycol powder is dissolved in a 1:1 mixed solution of the Step 1 solutions with a content of 10% at 80° C., to make it completely dissolved to be a clear solution;
Step 3: The mixed solution prepared in Step 2 is placed at room temperature for 30 minutes, then pouring it into a template, putting in a refrigerator at −18° C. for crosslinking, and taking it out of the refrigerator after freezing for 20 hours to obtain a hydrogel; circulating the freezing process for 4 times.

In Step 1, the molecular weight of polyvinyl alcohol is 120,000, and the viscosity of sodium alginate is 400 cP.

In Step 2, the molecular weight of polyethylene glycol is 1,500.

For the monolayer hydrogels prepared in the above Examples 1-9, the aperture sizes of the upper and lower surfaces of the freeze-dried samples are measured by scanning electron microscopy.

The type, viscosity and content of the tackifier used in the above Examples 1-9, the molecular weight and content of PVA, the molecular weight and content of PEG, the temperature of the warm mixed solution, and the time that the hydrogel preparation solution is placed at room temperature, the temperature and time for low-temperature freezing, and the aperture sizes of the upper surface/lower surface of the prepared hydrogel are summarized in Table 1 below.

Example 10

Step 1: Sodium carboxymethyl cellulose and polyvinyl alcohol are respectively dissolved in deionized water with a content of 2.4% and 22% to obtain the uniform clear solutions; polyethylene glycol powder is dissolved in a mixed solution of the above solutions with a content of 5.5% at 80° C., to make it completely dissolved to be a clear solution; and the mixed solution prepared above is placed at room temperature for 30 minutes, then pouring it into a template, putting in a refrigerator at −20° C. for 20 hours to obtain a monolayer hydrogel;

Step 2: Sodium carboxymethyl cellulose and polyvinyl alcohol are respectively dissolved in deionized water with a content of 2.0% and 18% to obtain the uniform clear solutions; polyethylene glycol powder is dissolved in a mixed solution of the above solutions with a content of 10.0% at 80° C., to make it completely dissolved to be a clear solution; and the mixed solution prepared above is placed at room temperature for 30 minutes, then pouring it

TABLE 1

| No. | Tackifier type/ Viscosity/ Content | PVA molecular weight/ Content | PEG molecular weight/ Content | Temperature of the warm mixed solution | Time at room temperature | Temperature/ time for low-temperature freezing | Aperture of the upper/ lower surface |
|---|---|---|---|---|---|---|---|
| 1 | Sodium carboxymethyl cellulose/ 5500 cP/3.2% | 80000/18% | 4000/7.0% | 80° C. | 80 min | −22° C./14 h | 10/80 |
| 2 | Sodium carboxymethyl cellulose/ 8000 cp/2.4% | 95000/28% | 1500/7.5% | 80° C. | 50 min | −22° C./6 h | 5/100 |
| 3 | Sodium carboxymethyl cellulose/ 9300 cp/1.4% | 100000/19% | 3000/10% | 90° C. | 10 min | −18° C./20 h | 15/95 |
| 4 | Hyaluronic acid/ 1000 cp/0.8% | 120000/22% | 2000/10% | 85° C. | 30 min | −18° C./20 h | 10/120 |
| 5 | Hyaluronic acid/ 800 cp/1.8% | 140000/19% | 1500/8.5% | 90° C. | 20 min | −22° C./18 h | 20/100 |
| 6 | Hyaluronic acid/ 600 cp/1.0% | 100000/24% | 4000/7.5% | 80° C. | 10 min | −18° C./20 h | 5/100 |
| 7 | Sodium alginate/ 600 cp/0.4% | 90000/19% | 3000/8.0% | 90° C. | 40 min | −20° C./22 h | 15/100 |
| 8 | Sodium alginate/ 800 cp/1.4% | 100000/24% | 2000/9.0% | 85° C. | 5 min | −22° C./16 h | 15/130 |
| 9 | Sodium alginate/ 400 cp/1.0% | 120000/20% | 1500/10% | 80° C. | 30 min | −18° C./20 h | 10/100 |

Observation shows that the mixed solution prepared in step 2 of the above examples is clear under warm conditions, but it becomes turbid, white and opaque after being left to cool. This is because PEG precipitates out of the solution and phase separation occurs. Under the teaching of this specification, those skilled in the art may control the aperture sizes of the hydrogel by adjusting the concentration, viscosity, and phase separation time.

Observation shows that the transparency of the monolayer hydrogel prepared in the above examples is good, and the wound healing may be observed in situ at any time without removing the dressing.

on the upper layer hydrogel obtained in Step 1 and thawed for 2 h, and putting in a refrigerator again at −20° C. for 20 hours to obtain a double-layer hydrogel.

In Step 1, the molecular weight of polyvinyl alcohol is 95,000, and the viscosity of sodium carboxymethyl cellulose is 7,000 cP, and the molecular weight of polyethylene glycol is 1,500.

In Step 2, the molecular weight of polyvinyl alcohol is 100,000, and the viscosity of sodium carboxymethyl cellulose is 7,300 cP, and the molecular weight of polyethylene glycol is 1,500.

FIG. 1 is a scanning electron micrograph of the monolayer hydrogel prepared in the examples. FIG. 1a is a scanning electron micrograph of the lower surface aperture size of a monolayer hydrogel with a loose structure; FIG. 1b is a scanning electron micrograph of the upper surface of a monolayer hydrogel with a dense structure; FIG. 1c is a scanning electron micrograph showing a longitudinal section of the monolayer hydrogel, and it can be seen that the aperture sizes of the hydrogel gradually increase from top to bottom in the thickness direction.

Figure 2:
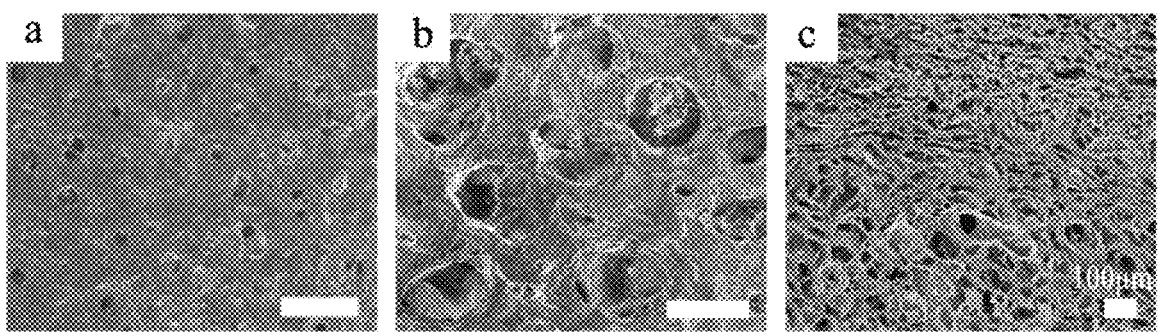
FIG. 2 is a scanning electron micrograph of the double-layer hydrogel prepared in the examples.

FIG. 2 is a scanning electron micrograph of the double-layer hydrogel prepared in the examples. FIG. 2a is a scanning electron micrograph of the upper surface aperture size of the double-layer hydrogel, and it can be seen that the aperture size is less than 20 μm and the structure is dense; and FIG. 2b is a scanning electron micrograph of the lower surface, and it can be seen that the aperture size is about 100 μm and the structure is loose; therefore, the upper and lower surfaces of the double-layer hydrogel have different aperture sizes. FIG. 2c is a scanning electron micrograph showing a longitudinal section of the double-layer hydrogel; it can be seen from this figure that the aperture sizes of the hydrogel gradually increase from top to bottom in the thickness direction, there are seamless butt joints between the two layers; and this is different from a stepped change of the aperture sizes between the two layers of a general double-layer hydrogel.

Figure 3:
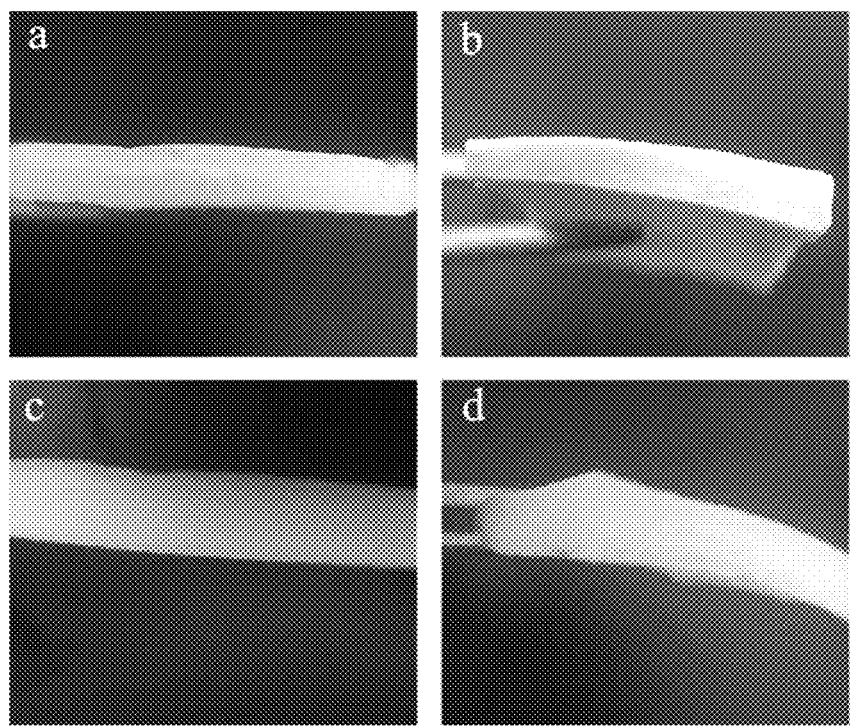
FIG. 3 is a photograph showing the morphology of the dry samples and the wet samples of the double-layer hydrogel prepared in the examples before and after shearing.

FIG. 3 is a photograph showing the morphology of the dry sample and the wet sample of the double-layer hydrogel prepared in the examples before and after shearing. It can be seen from this figure that, there is a good adhesion and no gap between the two layers of the dry and wet samples of the hydrogel before shearing; after being cut by scissors there is still a good adhesion between the wet and dry samples of the hydrogel, and they do not fall off due to external force. Therefore, the two layers of the prepared double-layer hydrogel are tightly bonded and are not easy to fall off.

The present invention has been described above through specific embodiments and examples, but those skilled in the art should understand that these are not intended to limit the scope of the present invention, and the scope of the present invention should be determined by the appended claims.

INDUSTRIAL APPLICABILITY

According to the present invention, provided is a polyvinyl alcohol hydrogel with excellent biocompatibility and functions including blocking bacteria, preventing adhesion, absorbing exudate, promoting wound healing, and observing wound healing process in situ.

The invention claimed is:

1. A method for preparing a monolayer hydrogel, comprising the following steps:
   (1) dissolving a water-soluble tackifier in water to obtain a water soluble tackifier aqueous solution and dissolving polyvinyl alcohol in water to obtain a polyvinyl alcohol aqueous solution; wherein the viscosity of the water-soluble tackifier is 200-10000 cP, and the content of the water-soluble tackifier in the water-soluble tackifier aqueous solution is 0.4 wt %-3.6 wt %;
   (2) preparing a warm mixed solution of the water-soluble tackifier aqueous solution and the polyvinyl alcohol aqueous solution;
   (3) dissolving polyethylene glycol powder into the warm mixed solution, so that the polyethylene glycol powder is completely dissolved to provide a clear solution, thereby obtaining a hydrogel preparation solution; and
   (4) pouring the hydrogel preparation solution into a template and performing low-temperature freezing to obtain the monolayer hydrogel,
   wherein the monolayer hydrogel has an asymmetric aperture size; and
   an aperture size of an upper surface of the monolayer hydrogel is 1-30 μm, an aperture size of a lower surface of the monolayer hydrogel is 50-300 μm, and aperture size in the monolayer hydrogel gradually increases from the upper surface to the lower surface.

2. The method according to claim 1, wherein the water-soluble tackifier is selected from the group consisting of: hyaluronic acid, sodium alginate, sodium carboxymethyl cellulose, chondroitin sulfate, and keratan sulfate.

3. The method according to claim 1, wherein the low-temperature freezing is performed at −14° C. to −24° C. for 6 to 30 hours.

4. The method according to claim 1, further comprising a step (3-1) of maintaining the hydrogel preparation solution at room temperature for 1-200 minutes, wherein step (3-1) is performed between step (3) and step (4).

5. A method for preparing a double-layer hydrogel, comprising the following steps:
   (a) preparing the monolayer hydrogel according to the method of claim 1;
   (b) preparing an additional hydrogel preparation solution according to steps (1)-(3); and
   (c) pouring the additional hydrogel preparation solution on the lower surface of the monolayer hydrogel prepared in the above step (a) in a normal temperature state, and then performing low-temperature freezing to obtain the double-layer hydrogel.

6. The method according to claim 5, wherein the low-temperature freezing in step (c) is performed at −14° C. to −24° C. for 6 to 30 hours.

7. A method for preparing a double-layer hydrogel, comprising the following steps:
   (a) preparing the monolayer hydrogel according to the method of claim 2;
   (b) preparing an additional hydrogel preparation solution according to steps (1)-(3); and
   (c) pouring the additional hydrogel preparation solution on the lower surface of the monolayer hydrogel prepared in the above step (a) in a normal temperature state, and then performing low-temperature freezing to obtain the double-layer hydrogel.

8. A method for preparing a double-layer hydrogel, comprising the following steps:
   (a) preparing the monolayer hydrogel according to the method of claim 3;
   (b) preparing an additional hydrogel preparation solution according to steps (1)-(3); and
   (c) pouring the additional hydrogel preparation solution on the lower surface of the monolayer hydrogel prepared in the above step (a) in a normal temperature state, and then performing low-temperature freezing to obtain the double-layer hydrogel.

9. A method for preparing a double-layer hydrogel, comprising the following steps:
   (a) preparing the monolayer hydrogel according to the method of claim 4;
   (b) preparing an additional hydrogel preparation solution according to steps (1)-(3); and
   (c) pouring the additional hydrogel preparation solution on the lower surface of the monolayer hydrogel prepared in the above step (a) in a normal temperature state, and then performing low-temperature freezing to obtain the double-layer hydrogel.

10. The method according to claim 7, wherein the low-temperature freezing in step (c) is performed at −14° C. to −24° C. for 6 to 30 hours.

11. The method according to claim 8, wherein the low-temperature freezing in step (c) is performed at −14° ° C. for 6 to 30 hours.

12. The method according to claim 9, wherein the low-temperature freezing in step (c) is performed at −14° C. to −24° C. for 6 to 30 hours.

13. The method according to claim 1, wherein the monolayer hydrogel is a sponge-like polyvinyl alcohol hydrogel.

* * * * *